(12) United States Patent
Mäntylä et al.

(10) Patent No.: US 6,998,021 B2
(45) Date of Patent: Feb. 14, 2006

(54) ARRANGEMENT FOR PAPER MACHINE, AND BLOW BOX

(75) Inventors: Markku Mäntylä, Kangasala (FI); Matti Kukkurainen, Tampere (FI); Jari Koivu, Tampere (FI)

(73) Assignee: Metso Automation Oy, Helsinki (FI)

(*) Notice: Subject to any disclaimer, the term of this patent is extended or adjusted under 35 U.S.C. 154(b) by 315 days.

(21) Appl. No.: 10/103,905

(22) Filed: Mar. 22, 2002

(65) Prior Publication Data

US 2002/0134523 A1   Sep. 26, 2002

(30) Foreign Application Priority Data

Mar. 23, 2001  (FI)  .................................. 20010603

(51) Int. Cl.
*D21F 7/06*   (2006.01)

(52) U.S. Cl. .............. 162/263; 162/272; 162/275; 162/198; 162/DIG. 10; 162/252; 162/253; 162/254; 162/255; 162/256; 162/257; 162/258; 162/259; 162/260; 34/446; 34/447; 34/448; 34/561; 34/114; 34/115; 34/116; 73/37.7; 73/159; 356/442; 356/336

(58) Field of Classification Search ............... 162/263, 162/272, 275, 198, DIG. 10, 252, 253, 254, 162/255, 256, 257, 258, 259, 260, 262; 34/446, 34/447, 484, 561, 114–123, 445, 455, 528, 34/529; 73/37.7, 159, 73; 356/442, 336
See application file for complete search history.

(56) References Cited

U.S. PATENT DOCUMENTS

| | | | | |
|---|---|---|---|---|
| 1,969,546 A | * | 8/1934 | Broughton | ................. 162/198 |
| 2,177,558 A | * | 10/1939 | Callan Jr. | ..................... 73/73 |
| 4,416,070 A | * | 11/1983 | Vedenpa et al. | ............... 34/114 |
| 5,245,200 A | * | 9/1993 | Fladda | ......................... 250/564 |
| 5,377,428 A | | 1/1995 | Clark | |
| 5,492,601 A | * | 2/1996 | Ostermayer et al. | ......... 162/198 |

FOREIGN PATENT DOCUMENTS

| | | |
|---|---|---|
| DE | 1120262 | 12/1961 |
| DE | 3216614 | 11/1982 |
| EP | 0692569 | 1/1996 |
| WO | WO-99/44015 | 9/1999 |
| WO | WO-99/55959 | 11/1999 |
| WO | WO-00/77498 | 12/2000 |
| WO | WO-01/32980 | 5/2001 |
| WO | WO-02/070819 | 9/2002 |

OTHER PUBLICATIONS

Rikka Gerlander; Kosteusprofiilin mittaus paperikoneen märässä päässaä (Moisture profile measuring at the wet end of a paper machine); Paperi ja Puu (Paper and Timber); vol. 82 No. Jun. 2000.

(Continued)

*Primary Examiner*—Mark Halpern
(74) *Attorney, Agent, or Firm*—Alston & Bird LLP

(57) ABSTRACT

In a paper machine which comprises process elements and a measuring beam, the measuring beam is arranged at least at one paper machine process element so that a measuring device for measuring quality properties of a paper web is arrangeable in the measuring beam. The paper machine process element is e.g. a blow box, which is arrangeable in a dryer unit of the paper machine between drying cylinders to blow air via at least one blow air channel provided in the blow box to guide the moving paper web and/or to assist drying.

27 Claims, 4 Drawing Sheets

OTHER PUBLICATIONS

Copy of Finnish Official Action for Appl. No. 20010603, dated Nov. 16, 2001.

Copy of International Search Report for PCT/FI02/00244 completed May 28, 2002.

* cited by examiner

ARRANGEMENT FOR PAPER MACHINE, AND BLOW BOX

This application claims priority over application 20010603 filed in Finland on 23 Mar. 2001.

BACKGROUND OF THE INVENTION

1) Field of the Invention

The invention relates to an arrangement for a paper machine, which comprises process elements, and the arrangement includes a measuring beam.

The invention further relates to a blow box which is arrangeable between drying cylinders in a dryer unit of a paper machine to blow air via at least one blow air channel provided in the blow box to guide a moving paper web and/or assist drying.

2) Description of Related Art

In paper manufacture quality properties of paper, such as moisture, thickness and basis weight, are measured as the paper web to be manufactured moves in the paper machine. Paper quality properties are most commonly measured by measuring devices, where measuring sensors are arranged in measuring carriages, which move to and fro in the cross direction of the paper web across its whole width. Since the paper web moves constantly forward, the measuring path of the sensors forms a 'zigzag' path, which makes it difficult to distinguish between CD, i.e. cross direction, paper properties and MD, i.e. machine direction, paper properties. Furthermore, generation of a paper cross profile on the basis of the measured properties requires numerous calculations. In addition, generation of the web cross profile is relatively slow because it typically takes several dozens of seconds before the measuring device has once traversed the width of the whole paper web. A measuring device of this kind which moves to and fro in the paper cross direction, i.e. a traversing measuring device, is described in WO 99/44015, for instance.

It is also known to measure the whole cross profile of the paper web by measuring devices, where several measuring sensors are arranged stationary along the whole width of the paper web for simultaneous measuring of the same property of parallel paper web sections. The paper cross profile can be formed very fast by a measuring device of this kind, but the problem associated with it is that a large number of measuring sensors are needed to cover the whole width of the paper web.

There are also prior art solutions where measuring sensors are arranged to move a distance corresponding to part of the paper web width in its cross direction. This is known as a mini-traversing measuring device. This mini-traversing measuring device provides the advantage that the number of adjacent measuring sensors needed to cover the whole width of the paper web is not that large and the paper web cross profile can be formed considerably more accurately and faster than with a measuring device which traverses the whole width of the paper web. An example of a mini-traversing measuring device is described in WO 00/77498.

A problem associated with the existing measuring devices is that in practice they can only be placed at the dry end of the paper machine, typically in the 'free space' between the dryer unit and the reeler, where there is enough room for the measuring frames needed to support the measuring devices. In the free space at the dry end the paper web travels unsupported and can thus be measured easily. In that case, however, reliable information is not obtained on the paper web properties at the wet end of the machine, e.g. on moisture at the press section. Consequently, it is considerably slower and more difficult to influence the paper web properties already at the wet end of the machine e.g. by changing the web moisture profile by controlling the press section.

Measuring of the paper web moisture profile immediately after the press section is described in *Kosteusprofiilin mittaus paperikoneen märässä päässä* (Moisture profile measuring at the wet end of paper machine), Riikka Gerlander, Paperi ja Puu—Paper and Timber Vol. 82/ no. 6/2000. According to the publication, the moisture profile of a paper web is measured by a measuring device which traverses the whole paper web width and is typically arranged to move in a measuring beam which has the same width as the web and is placed between the lower cylinders below the first dryer unit. The problem associated with the solution described in the publication is, however, that there is not enough room for a measuring beam between the lower cylinders below the first dryer unit if there is already a blow box, for example, placed in that space to improve runability of the paper machine and drying of the web. Thus the solution described in the publication prevents placement of the blow box between the lower cylinders, which considerably impairs runability of the machine and drying of the paper web. Furthermore, since measuring is performed immediately after the press section, there are still moisture differences in the z direction (depth) of paper, which causes measurement errors.

BRIEF SUMMARY OF THE INVENTION

The object of the present invention is to provide a new solution for placing a measuring beam of a measuring device for measuring quality properties of a moving paper web in a paper machine.

The arrangement of the invention is characterized in that the measuring beam is arranged at least at one process element of the paper machine so that a measuring device for measuring quality properties of the paper web is arrangeable in the measuring beam.

The blow box of the invention is characterized in that the blow box comprises a space for arranging the measuring beam of a measuring device for measuring quality properties of the paper web at the blow box.

The basic idea of the invention is that in a paper machine, which comprises process elements, there is a measuring beam arranged at a process element so as to allow arrangement of a measuring device for measuring quality properties of the paper web in the measuring beam. The idea of a preferred embodiment is that the process element of the paper machine where the measuring beam is arranged is a blow unit, such as a blow box, a steam box or a hood. The idea of a second preferred embodiment is that the process element of the paper machine where the measuring beam is arranged is a doctor blade. According to a third preferred embodiment of the invention, the measuring beam is arranged at the blow box so that the measuring device to be arranged in the measuring beam can be arranged to measure quality properties of the paper web when it is supported. According to a fourth embodiment of the invention, the blow air channel of the blow box is in the upper part of the blow box and the measuring beam is arranged in the upper part of the blow box opposite the blow air channel. According to a fifth preferred embodiment of the invention, the measuring device substantially simultaneously measures paper web properties at several points in the cross direction of the paper web. According to a sixth preferred embodiment of the invention, the measuring device to be arranged in the measuring beam is a mini-traversing measuring device.

An advantage of the invention is that an inexpensive and simple solution can be achieved by combining a process element of the paper machine and a measuring beam which alone take a lot of room. Thanks to the solution, the process element of the paper machine and the measuring device for measuring quality properties of the paper web can also be placed in a confined space in the paper machine. A solution which is advantageous in respect of the measuring technique can be achieved by arranging the measuring beam at the process element so that the measuring device to be arranged in the measuring beam measures paper web properties when the paper web is supported because the web is at a constant distance from the measuring device. When the measuring device is mini-traversing, the whole paper web width can be covered with a reasonable number of measuring channels.

Since the solution according to the invention is exactly the same in paperboard and tissue machines, the term 'paper' used in this description does not only refer to paper but also to paperboard and tissue. Similarly the term 'paper machine' also refers to a paperboard machine and a tissue machine.

BRIEF DESCRIPTION OF THE SEVERAL VIEWS OF THE DRAWINGS

The invention will be described in greater detail in the accompanying drawings, in which.

DETAILED DESCRIPTION OF THE INVENTION

Figure 1:
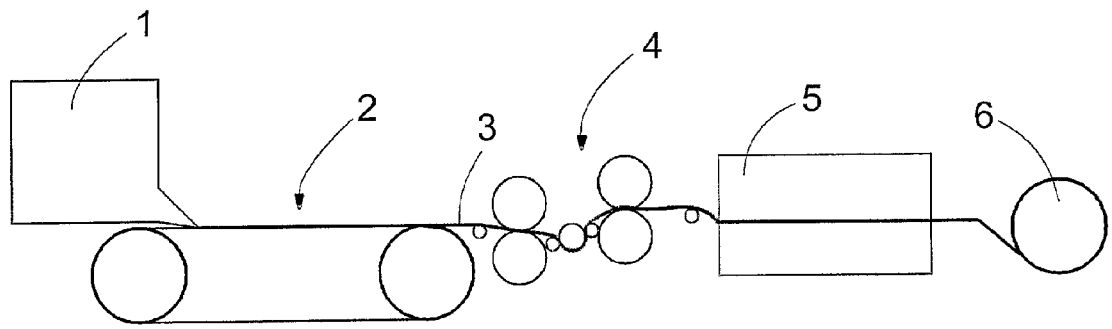
FIG. 1 is a schematic side view of a paper machine.

FIG. 1 schematically illustrates a paper machine. The paper machine comprises a head box 1, from which pulp is fed to a former 2, where a paper web 3 is formed from the pulp. The paper web 3 is guided to a press section 4 and further to a dryer unit 5. From the dryer unit 5 the web is guided to a reeler 6. The paper machine may also comprise other parts, e.g. a size press or a calender, which are not shown in FIG. 1 for the sake of clarity. The function of paper machine is also known per se to a person skilled in the art, for which reason it is not described more closely here.

Figure 2:
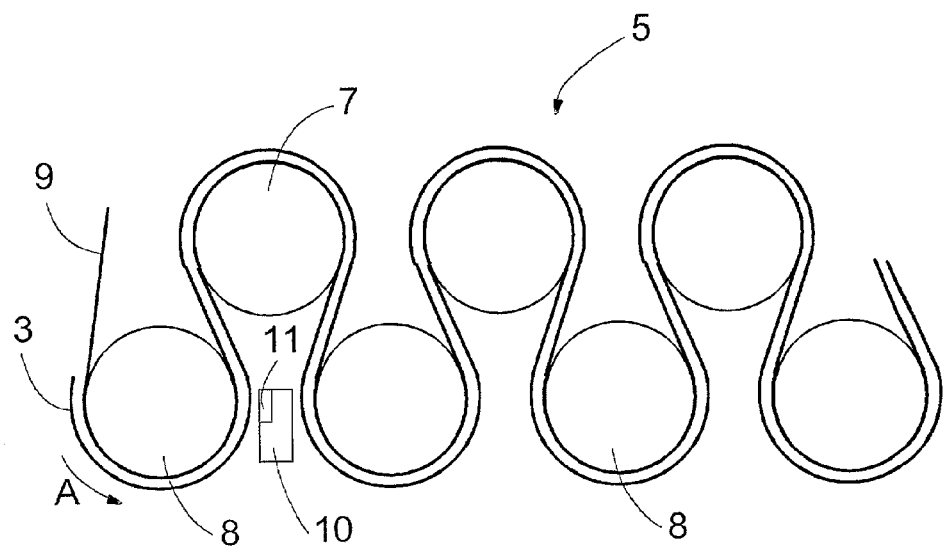
FIG. 2 is a schematic side view of a dryer unit of the paper machine.

FIG. 2 schematically illustrates the forward end of the dryer unit 5 of the paper machine 1. FIG. 2 shows some of the drying cylinders included in the dryer unit 5, i.e. steam-heated rolls 7 in the upper part of the dryer unit 5, and vacuum rolls 8 in the lower part of the dryer unit 5. The rolls in the lower part of the dryer unit 5 do not need to be vacuum rolls but they may also be conventional cold or heated rolls.

The dryer unit 5 typically comprises several dozens of steam-heated rolls 7 and vacuum rolls 8. FIG. 2 also shows a drying wire 9, which supports the paper web 3 as it moves. Instead of the drying wire 9, it is also possible to use a dryer felt or another similar drying fabric. In the vacuum rolls 8 there is low pressure which sucks the drying wire 9 and the paper web 3 against the roll. At the same time the moisture that passes through the drying wire 9 is sucked by the wire. In the steam-heated rolls 7 there is no similar suction. Furthermore, FIG. 2 schematically illustrates a blow box 10 placed between the vacuum rolls 8 at the forward end of the dryer unit 5. The blow box 10 is a runability component which is typically used at the forward end of the dryer unit 5 in faster machines to guide the paper web and remove moisture from it. The blow box 10 blows air towards an opening 32 formed by the drying cylinder 7 and the vacuum roll 8 to guide the travel of the paper web 3 from the cylinder 7 to the roll 8. The air blowing also assists paper drying. In FIG. 2, as also in FIG. 3, the paper web 3 direction is marked with arrow A. The basic structure and function of the blow box 10 are known per se to a person skilled in the art, for which reason they will not be discussed in greater detail in this application.

Figure 3:
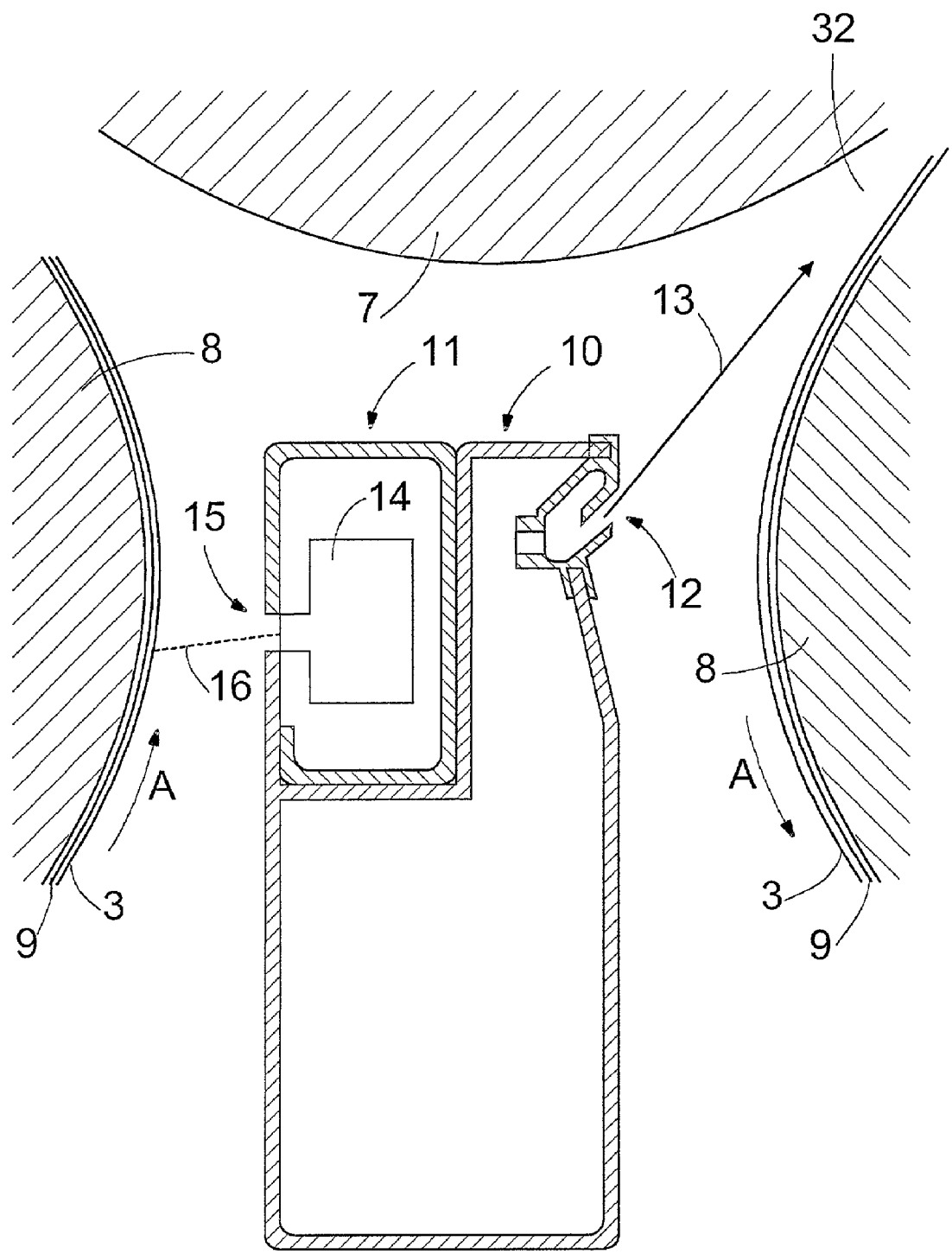
FIG. 3 is a schematic and cross-sectional view of an embodiment according to the invention for combining a blow box and a measuring beam, FIG. 4 schematically illustrates a measuring device from the web direction which can be arranged in a measuring beam arranged in a process element of the paper machine.

FIG. 2 schematically also illustrates a solution according to the invention where the measuring beam 11, which supports the measuring devices that measure the quality properties of paper, is arranged in the blow box 10. FIG. 3 is a more detailed cross sectional view of this solution where the blow box 10 is arranged between the two first vacuum rolls 8 of the dryer unit 5 as illustrated in FIG. 2. The blow box 10 and the measuring beam 11 in connection with it can in principle be arranged between the vacuum rolls 8 anywhere in the dryer unit 5. Furthermore, more than one blow box 10 can be arranged in the dryer unit 5, either with or without the measuring beam 11. To improve runability of the paper machine and to achieve the best measuring results, the blow box 10 and the measuring beam 11 are preferably placed between the second and the third vacuum rolls 8. In the upper part of the blow box 10 there is a blow air channel 12, from which airflow 13 is guided into the opening 32 formed by the drying cylinder 7 and the vacuum roll 8. Air blowing helps the paper web 3 to travel with the wire to the vacuum roll 8 and thus the paper web 3 does not follow the drying cylinder 7. In that case the air blowing improves the runability of the machine. In the blow box 10 there is a measuring beam 11 provided opposite the blow air channel 12. The measuring beam 11 is arranged in the blow box 10 by means of partial form locking between the blow box 10 and the measuring beam 11. The form locking can be secured with separate fastening means between the blow box 10 and the measuring beam 11. The measuring beam 11 shown in FIG. 3 is hollow and there is a measuring device arranged inside it for measuring quality properties of the paper web 3 by means of reflection measuring. The measuring device 14 emits measurement radiation 16 through a measuring window 15 towards the paper web 3. The measuring device 14 comprises measuring heads, which measure the part of the measurement radiation 16 that is reflected from the paper web 3. This can be used for determining desired quality properties of the paper web 3.

Figure 8:
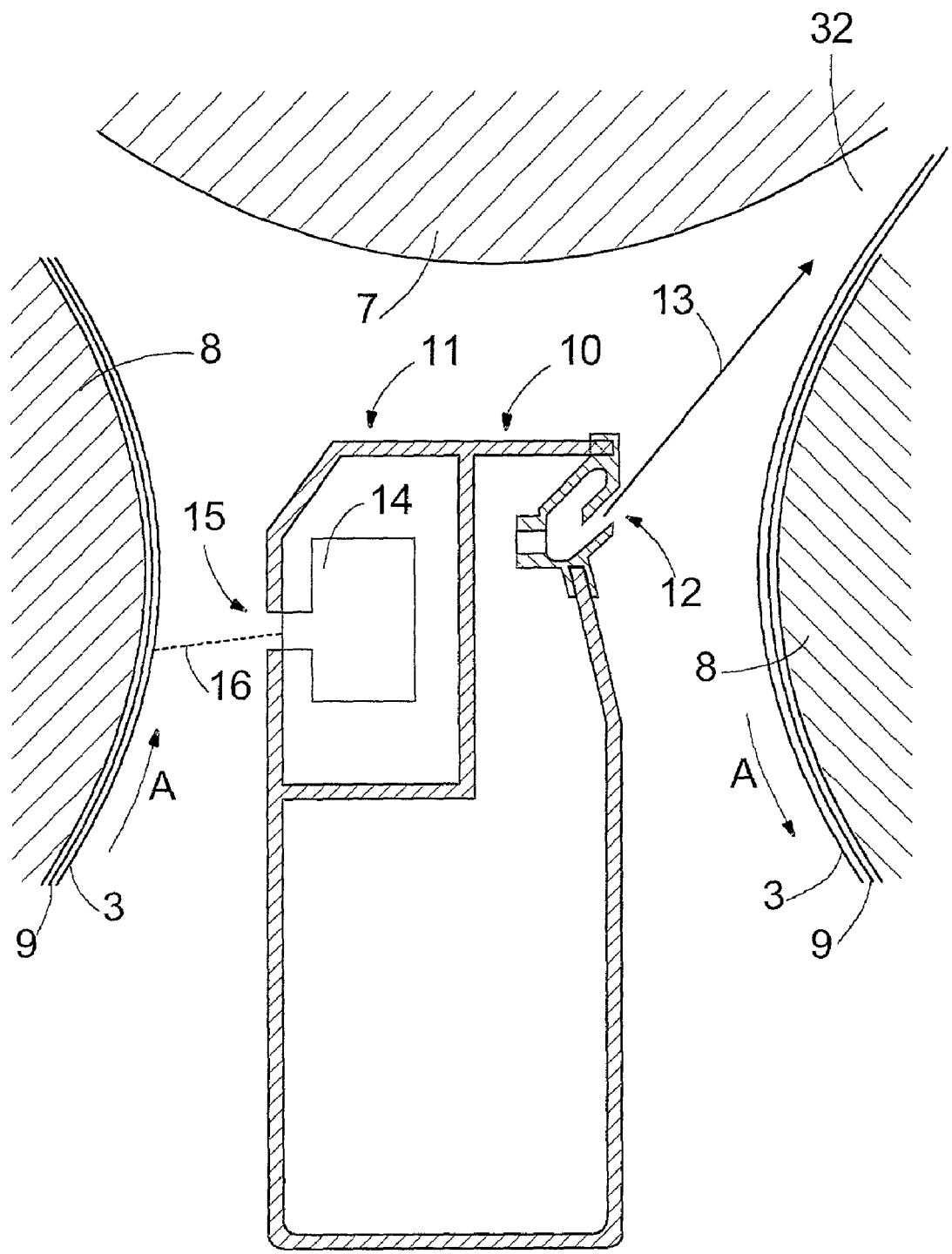
FIG. 8 is a schematic and cross-sectional view of a second arrangement of the invention for combining a blow box and a measuring beam.

In FIG. 3 the measuring beam 11 is arranged in the upper part of the blow box 10 opposite the blow air channel 12. The blow box 10 can, however, be implemented in various ways, in which case the measuring beam 11 can also be arranged in the blow box 10 in several different ways. Thus the measuring beam 11 can also be placed in the lower part of the blow box 10, either on the same side as the blow air channel 12 or on the opposite side. Preferably the measuring beam 11 is, however, arranged at the blow box 10 so as to allow arrangement of the measuring device 14 in the measuring beam 11 so that the measuring device 14 measures the quality properties of the paper web 3 where the paper web 3 is supported by the drying wire 9, which is supported by a vacuum roll 8. Thus the measuring device 14 can also be arranged to measure paper web 3 properties on the same side of the blow box 10 where the blow air channel 12 is. The blow box 10 and the measuring beam 11 can be integrated into one unit or separate parts which are arranged together or attached to each other. The blow box 10 and the measuring beam 11 most preferably form one single unit, i.e. these components are completely integrated. In that case it can be said that the measuring beam includes the features of the blow box. When integration is complete, the component in question can also be defined by saying that there is a measuring beam in the blow box. In other words, in the solution according to the invention the process element of the paper machine is most preferably part of the measuring beam or the measuring beam is part of the process element of the paper machine. FIG. 8 schematically illustrates a solution where the blow box 10 and the measuring beam 11 form one single unit, i.e. these components are completely integrated. In that case the measuring beam 11 is a fixed part of the blow box 10.

Figure 5:
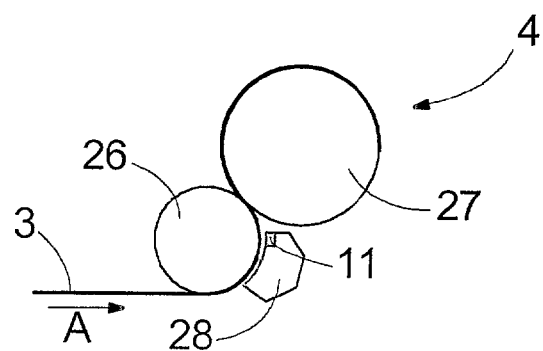
FIG. 5 is a schematic side view of a press section of the paper machine.

The invention is also applicable to paper machine process elements other than the blow box. FIG. 5 illustrates part of a press section 4. The press section 4 includes a press suction roll 26 and a middle roll 27. There is a steam box 28 provided with a measuring beam 11 arranged against the press suction roll 26.

Figure 6:
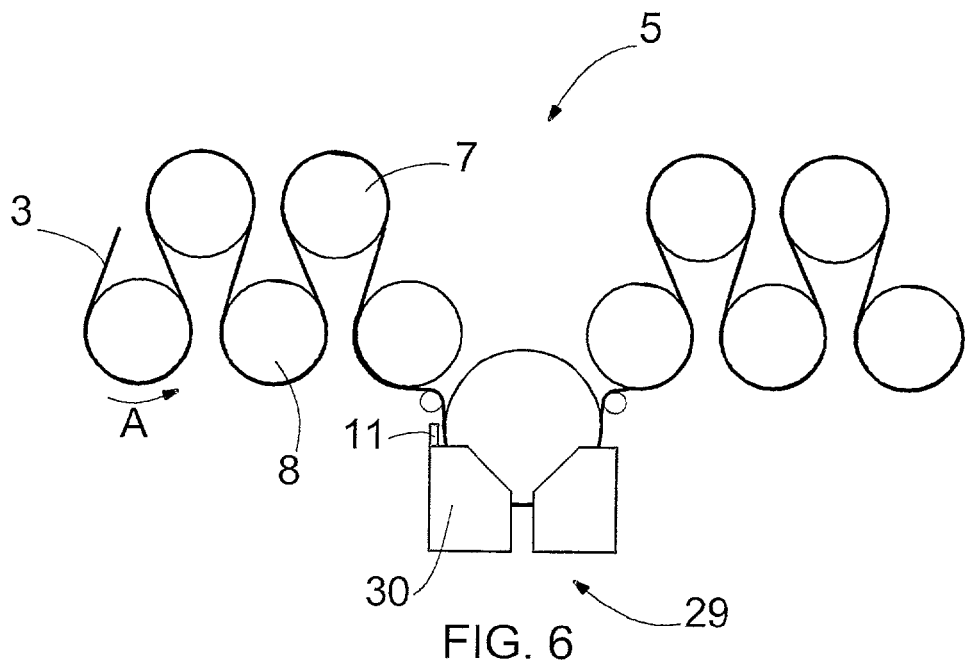
FIG. 6 is a schematic side view of a second dryer unit of the paper machine.

FIG. 6 shows a solution where an air impingement unit 29 is arranged in the dryer section of the paper machine. The air impingement unit 29 includes a hood 30, which is provided with a measuring beam 11.

Figure 7:
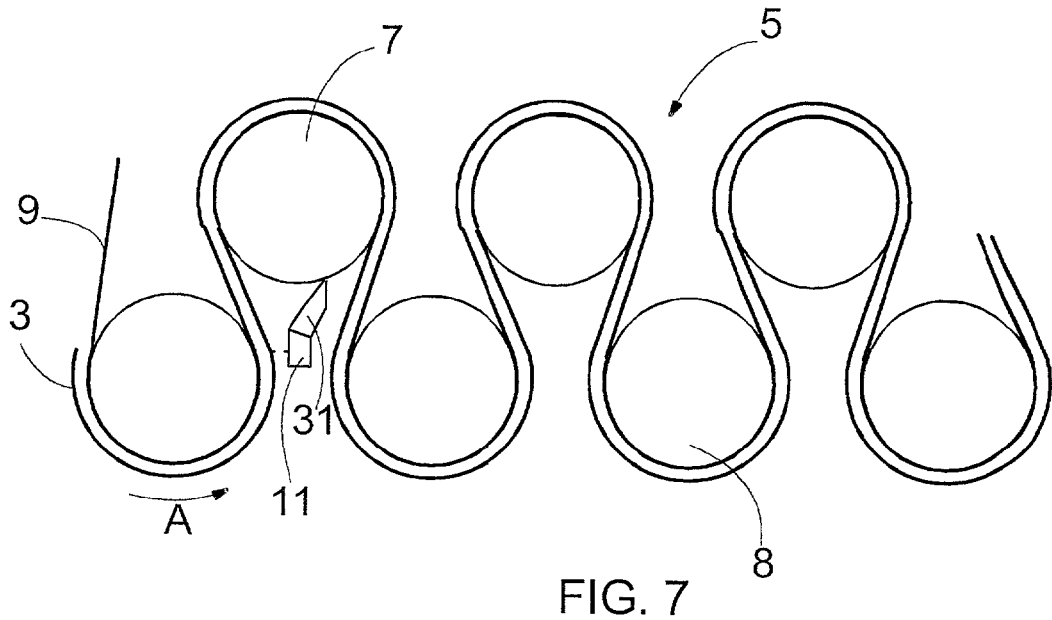
FIG. 7 is a schematic side view of a third dryer unit of the paper machine.

FIG. 7 illustrates a dryer unit 5 of the paper machine where a doctor blade 31 is arranged in connection with the drying roll. The doctor blade 31 is provided with a measuring beam 11.

An advantage of the invention is that by designing a process element compatible with a measuring beam 11, it is possible to achieve a sufficiently compact solution which allows optimization of the use of the narrow space in the paper machine and combines good runability of the paper web 3 and measuring of the paper web 3 properties at the wet end. The measuring beam 11 alone takes up a lot of space, as well as different process elements. Thus combining the process element 10 and the measuring beam 11 enables placement of the measuring beam in a confined space, e.g. in the space between the vacuum rolls 8. The process elements provide the measuring beam 11 with a sufficiently rigid base to which it can be attached without impairing the function of the process elements in any way.

When the blow box arrangement shown in FIGS. 2 and 3 is used, the placement of the measuring beam 11 at the beginning of the dryer section 5 is advantageous in respect of the measuring technique because the surrounding conditions are easier than inside the press section 4. When the measuring beam 11 is arranged in the blow box 10 so that the measuring device 14 to be arranged in the measuring beam 11 measures the paper web 3 properties where the paper web 3 is supported by the drying wire 9 and the vacuum roll 8, the distance between the paper web 3 and the measuring device 14 does not change, which makes it easier to plan measuring. Furthermore, it is unnecessary to arrange free draw for measuring.

Figure 4:
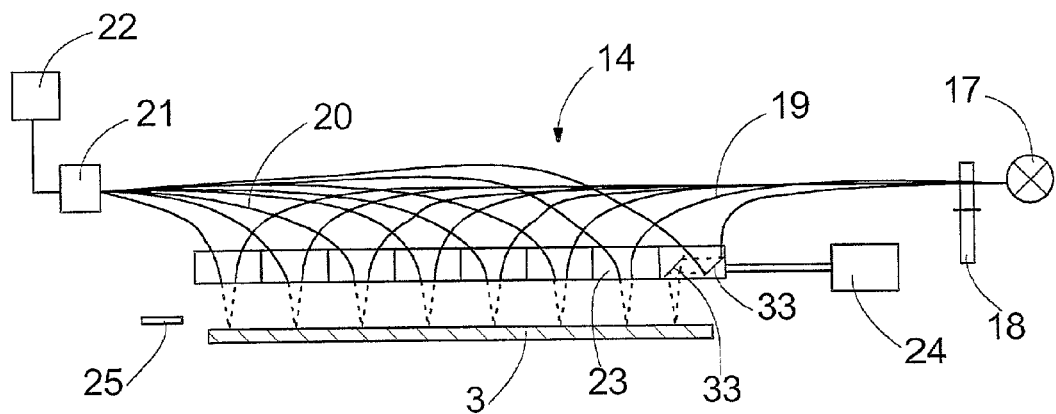

FIG. 4 schematically illustrates the structure and operating principle of a measuring device 14 whose space requirements make its arrangement in the measuring beam 11 provided in the blow box 10 simple and easy. The measuring device 14 comprises a radiation source 17, which emits radiation preferably in the infrared area. The wavelength of radiation may be e.g. between 1 and 2.5 $\mu$m, but if necessary, the wavelength can be outside the above-mentioned range. The radiation source 17 may be e.g. a halogen lamp or a Planckian radiator or another suitable radiation source. After the radiation source 17 there is a chopper 18, which cuts the radiation emitted by the radiation source 17 in a manner known per se. The radiation is carried to the paper web 3 with first optical fibers 19. The radiation reflected from the paper web 3 is carried further to a spectrometer 21 with second optical fibers 20. Both the ends of the first optical fibers 19 and the ends of the second optical fibers 20 are arranged at the measuring heads 23. The measuring heads 23 can also be provided with the necessary measuring optics, e.g. with lenses or mirrors or the like. The distance of the measuring heads 23 from the paper web 3 may be in the range of 10 cm.

From the spectrometer 21 the measuring information is fed to a data processing unit or a control unit 22. The spectrometer 21 is an imaging spectrometer, i.e. it images the spectrum of the measuring point. Here a spectrometer refers to a measuring device which comprises at least a spectrograph, preferably an imaging spectrograph, and a matrix detector. The spectrograph divides the radiation carried by the fiber into different wavelengths for the matrix detector. The imaging spectrograph may be e.g. a PGP-type spectrograph, a grid spectrograph or another suitable spectrograph. Since measuring information is supplied simultaneously from several measuring points with the second optical fibers 20, the device determines the infrared spectrum reflected from the paper web 3 from several measuring points at the same time, i.e. the measuring device 14 measures the paper web 3 properties substantially simultaneously at several points in the cross direction of the paper web 3. The apparatus produces a matrix which shows the place of each measuring point and information on the spectrum. The spectrum is preferably measured in the near infrared area, e.g. in the range of 1.0 to 1.7 $\mu$m or 1.0 to 2.4 $\mu$m. The infrared light is scattered into a spectrum with a spectrograph and the scattered light is measured with a matrix detector. The spectrograph and the matrix detector are not shown separately in FIG. 4. Information from each optic fiber arrives at a specific point on the location axis of the spectrograph. The information of each point is dispersed onto the matrix detector at a specific point on the location axis so that the light is spread onto the spectrum axis.

Each measuring head 23 and optical fiber 20 form a single measuring channel and as many measuring channels as necessary can be arranged in parallel. If the channel resolution is e.g. 5 mm in the machine cross direction and substantially each point of a 10-meter-wide paper web 3 is to be covered, 2000 measuring points, i.e. measuring channels, are needed. However, the measuring heads 23 can be made to move to and fro a distance corresponding to part of the paper web 3 in the cross direction by an oscillating means 24. By moving the measuring heads 23 to and fro 10 cm, for instance, substantially each point of the above-mentioned 10-meter-wide paper web can be measured using hundred measuring channels. Such a short movement does not subject the fibers 19 and 20 to a considerable mechanical stress. In that case the number of measuring channels needed can be reduced considerably; yet the measurement can be performed along the whole width of the paper web 3 e.g. in less than a second, whereas nowadays traversing from one edge of the paper web to the other typically takes dozens of seconds. When the to and fro movement is made slightly longer than the distance between the channels, i.e. slightly longer than 10 cm in the above case, adjacent measuring points also measure the same cross-directional position of the paper web 3, i.e. the measuring channels partly overlap. This measuring of the same point can be utilized e.g. in standardization of measuring channels or even in transmission of configuration.

The measuring device 14 further comprises a moving reference unit 25, which can be moved across the path of the measurement radiation of all measuring channels. In that case the same reference/standardization board is used for standardization of all measuring channels. In the reflection measurement shown in FIG. 4 the measuring device 14 can be standardized during paper manufacture, i.e. the reference unit 25 is arranged to move between the measuring heads 23 and the paper web 3.

The arrangement of a mini-traversing measuring device 14 shown in FIG. 4 for use in a measuring beam 11 arranged at a process element, e.g. a flow box 10, is very advantageous because it needs very little space. The measuring device 14 can be arranged in the measuring beam 11 e.g. by arranging only the optical fibers 19 and 20 and the measuring heads 23 in the measuring beam. The measuring arrangement inside the measuring head 23 is preferably implemented by mirror optics, in which case the mirrors 33 provided inside the measuring head 23 can be used for adjusting the path of the measuring beam inside the measuring head 23 to travel partly in the depth direction of the measuring head 23 and partly in the lateral direction. Thanks to this, the measuring arrangement can be made very narrow and thus the measuring beam and the measuring device can be arranged in a very confined space at the blow box. For the sake of clarity, FIG. 4 illustrates only the mirror optics arranged inside the outermost measuring head 23 but naturally the mirror optics is in practice arranged inside each measuring head 23. The other parts of the apparatus, such as light source, chopper, spectrometer and control unit, can be placed separately in suitable places near the paper machine, provided that the fibers are connected to these devices. Instead of the imaging spectrometer 21, an infrared line camera can be used and the wavelengths of the measuring points can be separated with interference filters arranged in a rotating filter disc, for instance. The measuring device 14 can be used for measuring the moisture, dry weight, ash content or another property of the paper web 3.

The drawings and the related description are only intended to illustrate the inventive concept. The details of the invention may vary within the scope of the claims. Thus the size and shape of the blow box 10 and the measuring beam 11 may vary in several ways. The measuring device to be arranged in the measuring beam can also be fixed or a measuring device which traverses across the whole width of the paper web. Preferably, however, the measuring device is a mini-traversing measuring device similar to the one shown in FIG. 4. The dryer unit 5 can also be implemented in various ways, e.g. the steam-heated rolls 7 can be arranged in the lower part of the dryer unit 5 and the vacuum rolls 8 in the upper part of the dryer unit 5. Furthermore, the dryer unit does not need to comprise any vacuum rolls but all the rolls can be conventional ones. The structure of the dryer unit may also differ from the one shown in the figures, i.e. the dryer unit may be any kind of paper machine dryer unit known per se. The process element of the paper machine where the measuring beam is arranged can be any element that influences either the paper web properties, such as a blow unit, or the paper machine operation, such as a doctor blade. Thus the paper machine process element concerned is not limited to a blow unit or a doctor blade. The blow unit can be a blow box, steam box or a hood, for example, or another blow unit which contributes to drying of the paper by means of the medium it blows and/or to the paper travel in the paper machine. The entity that includes the process element of the paper machine and the measuring beam can be placed elsewhere than in the dryer unit or press unit. This entity may be arranged e.g. in an on-line coating unit or in an off-line coating unit in a finishing machine. The term 'paper machine' thus covers all the devices involved in the manufacture and processing of paper, whether arranged on the same on-line production line or separately.

What is claimed is:

1. An arrangement for a paper machine including process elements configured to act on a paper web during the manufacture thereof, the arrangement including a measuring beam configured to support a measuring device, the measuring beam being mounted to one of the process elements acting on a side of the paper web for the measuring device to measure a quality property of the paper web when the paper web is supported, through direct interaction between the measuring device and the paper web, in proximity to, and with respect to the same side of the paper web as, the one process element and to provide a compact paper machine.

2. An arrangement according to claim 1, wherein the paper web is supported by a drying fabric.

3. An arrangement according to claim 2, wherein the drying fabric is supported by a drying cylinder.

4. An arrangement according to claim 1, wherein the process element of the paper machine where the measuring beam is arranged is a blow unit.

5. An arrangement according to claim 4, wherein the blow unit is a steam box.

6. An arrangement according to claim 4, wherein the blow unit is a hood.

7. An arrangement according to claim 4, wherein the blow unit where the measuring beam is arranged is a blow box.

8. An arrangement according to claim 7, wherein the paper machine comprises a dryer unit, which comprises drying cylinders for drying a moving paper web, and that the blow unit where the measuring beam is arranged is a blow box which is arranged between the drying cylinders and is provided with at least one blow air channel via which the blow box is arranged to blow air to guide the paper web and/or assist drying.

9. An arrangement according to claim 7, wherein the blow air channel of the blow box is arranged in the upper part of the blow box and the measuring beam is arranged in the upper part of the blow box opposite the blow air channel.

10. An arrangement according to claim 1, wherein the process element of the paper machine where the measuring beam, is arranged is a doctor blade.

11. An arrangement according to claim 1, wherein the process element of the paper machine and the measuring beam are integrated into one single unit.

12. An arrangement according to claim 1, wherein the measuring beam is hollow and the measuring device is arrangeable inside the measuring beam.

13. An arrangement according to claim 1, wherein the measuring beam is arranged to measure paper web properties substantially simultaneously at several points in the cross direction of the paper web.

14. An arrangement according to claim 1, wherein the measuring device is a mini-traversing measuring device.

15. An arrangement according to claim 1, wherein the measuring device comprises optical fibers for carrying measuring radiation for measuring the paper web properties.

16. An arrangement according to claim 15, wherein the measuring device comprises measuring heads and that substantially only the optical fibers and measuring heads of the measuring device components are arranged in the measuring beam.

17. An arrangement according to claim 1, wherein the measuring device comprises measuring heads, inside of which mirror optics are arranged for adjusting the path of the measurement radiation inside the measuring head to travel partly in the depth direction of the measuring head and partly in the lateral direction of the measuring head.

18. A blow box which is arrangeable in a dryer unit of a paper machine between drying cylinders to blow air via at least one blow air channel provided in the blow box to guide a moving paper web and/or assist drying, the blow box comprising a measuring beam having a measuring device mounted thereto, the measuring device being configured to measure quality properties of the paper web in proximity to the blow box.

19. A blow box according to claim 18, wherein the blow air channel of the blow box is arranged in the upper part of the blow box and that the space for arranging the measuring beam at the blow box is arranged in the upper part of the blow box opposite the blow air channel.

20. A blow box according to claim 18, wherein, the blow box and the measuring beam are integrated into a single unit.

21. A blow box according to claim 18, wherein the measuring beam is hollow and the measuring device is arrangeable inside the measuring beam.

22. A blow box according to claim 18, wherein the measuring device is arranged to measure the paper web properties substantially simultaneously at several points in the cross direction of the paper web.

23. A blow box according to claim 18, wherein the measuring device to be arranged in the measuring beam is a mini-traversing measuring device.

24. A blow box according to claim 18, wherein the measuring device comprises optical fibers for carrying measuring radiation for measuring the paper web properties.

25. A blow box according to claim 24, wherein the measuring device comprises measuring heads and that substantially only the optical fibers and measuring heads of the measuring device components are arranged in the measuring beam.

26. A blow box according to claim 18, wherein the measuring device comprises measuring heads, inside of which mirror optics are arranged for adjusting the path of the measurement radiation inside the measuring head to travel partly in the depth direction of the measuring head and partly in the lateral direction of the measuring head.

27. An arrangement for a paper machine including process elements configured to act on a paper web during the manufacture thereof, the arrangement including a hollow measuring beam configured to support a measuring device inside the measuring beam, the measuring beam being mounted to one of the process elements acting on a side of the paper web for the measuring device to measure a quality property of the paper web, through direct interaction between the measuring device and the paper web, in proximity to, and with respect to the same side of the paper web as, the one process element and to provide a compact paper machine.

* * * * *